United States Patent [19]

Carter

[11] 4,385,196

[45] May 24, 1983

[54] LIQUID-LIQUID EXTRACTION OF LOW BOILING OLEFIN CONTAINED IN OLEFIN-PARAFFIN MIXTURE USING SULFOLANE-KETONE SOLVENT SYSTEM

[75] Inventor: Cecil O. Carter, Bartlesville, Okla.

[73] Assignee: Phillips Petroleum Company, Bartlesville, Okla.

[21] Appl. No.: 264,310

[22] Filed: May 18, 1981

[51] Int. Cl.$^3$ ............................ C07C 7/00; C07C 7/10; C10G 21/28; C10G 21/12

[52] U.S. Cl. .................................. 585/864; 585/865; 585/857; 208/321; 208/325; 208/337

[58] Field of Search ...................... 585/865, 864, 857; 208/325, 332, 321

[56] References Cited

U.S. PATENT DOCUMENTS

| | | | |
|---|---|---|---|
| 2,096,950 | 10/1937 | Wilson | 208/321 |
| 2,357,344 | 9/1944 | Morris et al. | 208/325 |
| 2,360,859 | 10/1944 | Evans et al. | 208/325 |
| 2,360,861 | 10/1944 | Pierotti et al. | 208/325 |
| 3,634,537 | 1/1972 | Hutto | 585/865 |
| 3,864,244 | 2/1975 | Van Tassell | 208/321 |
| 3,996,113 | 12/1976 | Henneberg | 203/58 |
| 4,024,028 | 5/1977 | Haskell | 585/857 |
| 4,076,595 | 2/1978 | Haskell | 585/865 |
| 4,166,771 | 9/1979 | Haskell | 585/857 |

FOREIGN PATENT DOCUMENTS 998600  7/1965  United Kingdom ................ 208/325

*Primary Examiner*—Delbert E. Gantz
*Assistant Examiner*—Helane E. Maull

[57] ABSTRACT

A solvent system composed essentially of sulfolane and a ketone, e.g., sulfolane and methyl ethyl ketone is employed in a liquid-liquid extraction operation to separate a low boiling olefin, e.g., pentene-2, hexene-1, octene-1, etc., from a corresponding close boiling paraffin, e.g., n-pentane, n-hexane, and n-octane, respectively, and wherein solvent is recovered by employing a portion thereof in a drying or stripping column.

5 Claims, 1 Drawing Figure

LIQUID-LIQUID EXTRACTION OF LOW BOILING OLEFIN CONTAINED IN OLEFIN-PARAFFIN MIXTURE USING SULFOLANE-KETONE SOLVENT SYSTEM

BRIEF SUMMARY OF THE INVENTION

A low boiling olefin, e.g., pentene-2, hexene-1, octene-1, is separated from a close-boiling paraffin, e.g., n-pentane, n-hexane, and n-octane, respectively, employing a solvent system composed essentially of sulfolane and a ketone, e.g., methyl ethyl ketone, methyl n-propyl ketone, n-isopropyl ketone, etc.

DESCRIPTION OF DRAWING

The drawing shows an embodiment of a liquid-liquid extraction according to the invention including a regeneration of the solvent system which has beeen used.

DETAILED DESCRIPTION

Figure 1:
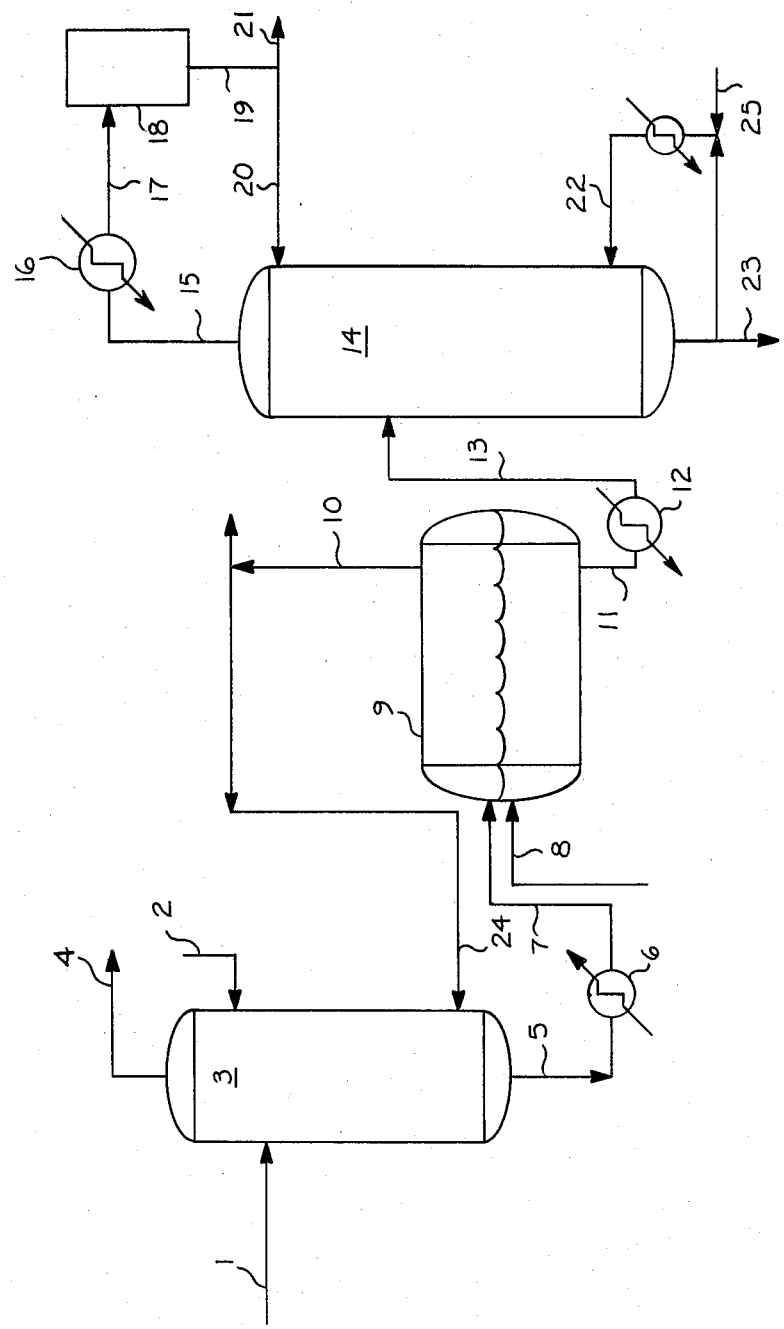

This invention relates to the separation of a low boiling olefin from its admixture with a corresponding low boiling paraffin. In one of its aspects the invention relates to a liquid-liquid solvent extraction system and to regeneration of solvents employed therein. In a more specific aspect of the invention it relates to the separation of a low boiling olefin of the nature of those herein set forth from a corresponding low boiling paraffin of the nature as herein set forth.

In one of its concepts the invention provides a solvent system especially adapted for the separation of a low boiling olefin from a corresponding low boiling paraffin, the system being composed of sulfolane and at least one ketone of the nature as herein described. In another of its concepts the invention provides, in one embodiment, a solvent extraction system and regeneration of solvent employed wherein a solvent composed essentially as herein described is contacted in countercurrent flow with the olefin-paraffin mixture to be separated, the solvent being introduced in a manner to flow essentially upwardly countercurrent to downwardly flowing olefin-paraffin mixture, the operation forming an extract phase and a raffinate phase, the raffinate phase recovered as a lower phase and containing principally paraffin, and an extract phase containing principally olefin with only a small amount of paraffin.

For many petrochemical operations, and other operations as known in the art, it is essential to recover olefin feedstocks. These feedstocks should be as free of paraffin as possible. Further, for other uses it is essential to recover substantially olefin-free paraffins. As known, olefins can be polymerized and otherwise reacted or interreacted to form valuable products. Paraffins can be converted to form additional olefins or used as such, e.g., as solvents or as chemical intermediates as in halogenation operations.

It is an object of this invention to set forth a method for the separation of a low boiling olefin and a low boiling paraffin. It is another object of the invention to recover by way of a liquid-liquid solvent extraction a low boiling olefin from a corresponding low boiling paraffin. In a further object of the invention set forth a solvent system for the separation of low boiling olefin from a corresponding low boiling paraffin. A still further object of the invention is to set forth the unitary process for operation in which a solvent system is employed to separate a low boiling olefin from a low boiling paraffin, the solvent is recovered, regenerated and reused.

Other aspects, concepts, objects and the several advantages of the invention are apparent from a study of this disclosure, the drawing and the appended claims.

According to the present invention there is provided a method for the separation of a low boiling olefin from a low boiling paraffin by a liquid-liquid solvent extraction employing a solvent system essentially composed of sulfolane and a ketone.

Mixtures which can be separated include olefins such as pentene-2, hexene-1, octene-1, etc. The corresponding paraffins from which such olefins can be recovered, respectively, include n-pentane, n-hexane, and n-octane, etc.

The ketone portion of the solvent now preferred is substantially composed of methyl ethyl ketone. Other ketones are useful together with MEK or as such are methyl n-propyl ketone (2-pentone), n-isopropyl ketone and the like.

Table I shows results of five experiments. Each experiment starts with a feed composition of 48.4 wt. % $C_8^= -1$ and 47.2 wt. % $nC_8$. The mixed solvent can contain about 40–90% sulfolane in the sulfolane-methyl ethyl ketone mixture.

TABLE I

| Solvent Sulfolane wt. % | Methyl Ethyl Ketone wt. % | S/F Wt. Ratio | Selectivity B | Solvent to Top Phase Wt. % | HC in Bottom Phase Wt. % |
|---|---|---|---|---|---|
| 69.7 | 30.3 | 1.40 | 1.76 | 11.1 | 6.2 |
| 49.8 | 50.2 | 1.39 | 1.47 | 20.7 | 14.5 |
| 79.0 | 21.0 | 5.1 | 1.82 | 3.7 | 3.1 |
| 62.0 | 38.0 | 4.5 | 1.48 | 6.1 | 8.9 |
| 40.2 | 59.8 | 1.4 | 1.22 | 61.0 | 6.9 |

Referring now to the drawing, a feed composed of approximately 25 wt. % octene-1 and about 75 wt. % n-octane is fed by 1 into extraction vessel 3. Solvent consisting essentially of approximately 70 wt. % sulfolane and approximately 30 wt. % MEK is introduced by 2 into countercurrent extraction thus producing at 4 a raffinate phase composed largely, for the hydrocarbon portion, of normal octane. A small quantity of octene-1 is present in the raffinate. A bottom 5 extract phase is taken off from vessel 3 and is composed for the hydrocarbon portion thereof principally of octene-1 and a small amount of normal octane. After a temperature adjustment, as may be needed, the extract phase is passed by 7 into separator 9 in which it is contacted with water introduced at 8.

Olefin recovered from the extract phase is removed at 10. A portion can be refluxed to extractor 3 by way of 24. Water-diluted solvent is withdrawn from separator 9, heated appropriately in heater 12 and fed by 13 to drying column 14. Solvent mixture of sulfolane and MEK is recovered at 23 for reuse. Stripping vapor or vaporous MEK is passed by 22 into the bottom of drying column 14. A vaporous stream 15 composed of MEK and water is passed by 15 and cooler 16 to the accumulator 18 a part of the condensed stream is passed by 19 and 20 to reflux the top of tower 14. The other part is taken off at 21.

The following is a calculated example (see FIG. 1) in which feed stream containing octene-1 and normal octane is passed to the extraction vessel at upper mid-section to flow in a countercurrent relationship to the solvent mixture of sulfolane and methyl ethyl ketone pumped in at the top of the extractor. Solvent and olefin mixture is then passed to the separator where water is added to phase separate olefin from solvent. Olefin is separated and recovered as product; the wet solvent is dried in a drying column using methyl ethyl ketone as stripping vapor. The solvent mixture of sulfolane and methyl ethyl ketone is recovered at the bottom of the column for recycle.

1. Feed: 100 lb/hr., 79° F., 35 psia
    Compositions:
    $C_8$=25 wt. %
    $nC_8$ 75 wt. %
2. S/F (Solvent/feed) wt. ratio 38.2
    Solvent: 3820 lb/hr., 79° F., 35 psia
    Compositions:
    sulfolane 70 wt. %
    methyl ethyl ketone 30 wt. %
3. Extractor:
    upper section 79° F., 35 psia
    lower section 82° F., 37 psia
    17 stages
4. Raffinate phase 92.7 lb/hr., 79° F., 35 psia
    Compositions:
    $C_8$=0.3 wt. %
    $nC_8$ 81.7 wt. %
    solvent 18.0 wt. %
    Solvent Free:
    $C_8$=0.39 wt. %
    $nC_8$ 98.61 wt. %
5. Extract phase 4067 lb/hr., 79° F., 35 psia
    Compositions:
    $C_8$=6.09 wt. %
    $nC_8$ 0.39 wt. %
    solvent 93.52 wt. %
    Solvent Free:
    $C_8$=94 wt.%
    $nC_8$6 wt. %
6. Heater
7. Portion of extract phase leaving heater 4067 lb/hr., 79° F.
8. $H_2O$ to separator 331 lb/hr. 79° F.
9. Separator 79° F. 35 psia
10. Olefins withdrawn from separator, 263 lb/hr., 79° F.
11. Water and solvent mixture 4133 lb/hr., 79° F.
    Compositions: $H_2O$ 8 wt. %, sulfolane 64.7 wt. %, ketone 27.3 wt. %
12. Heater 350,000 Btu/hr.
13. Water and solvent mixture leaving heater 4133 lb/hr., 232° F., 35 psia
14. Drying column: 20 stages
    Upper section 232° F., 34 psia
    Lower section 235° F., 36 psia
15. Overhead solvent mixture of water and methyl ethyl ketone 1986 lb/hr., 232° F., 34 psia
16. Cooler 1,865,251 Btu/hr.
17. Solvent leaving cooler 230° F.
18. Accumulator
19. Condensed water and solvent 1986 lb/hr., 230° F., 34 psia
20. Reflux 993 lb/hr.
21. Water and MEK 993 lb/hr.
22. Stripping vapor (methyl ethyl ketone) 18650 lb/hr., 235° F., 36 psia
23. Recovered solvent for recycle, bottom product from column, 3820 lb/hr., 235° F., 36 psia
24. Reflux 239 lb/hr., 79° F.
25. MEK Recycle 679 lb/hr.

Reasonable variation and modification are possible within the scope of the foregoing disclosure, the drawing and the appended claims to the invention, the essence of which is that there has been set forth a solvent system and a modus operandi wherewith to separate a low boiling olefin from a corresponding low boiling paraffin from which ordinarily the olefin is not separable by ordinary distillation techniques, the solvent system being composed essentially of sulfolane and a ketone and the modus operandi involving a liquid-liquid extraction to produce an extract containing the olefins, which is recovered from the extract by adding an anti-solvent such as water, and wherein solvent is regenerated as by stripping, as with a portion thereof, the water or other anti-solvent therefrom so that the solvent can be reused.

I claim:

1. A method for the separation of a low boiling olefin from a corresponding low boiling paraffin which comprises the steps of
    (a) passing a hydrocarbon feed comprising low boiling olefins and corresponding low boiling paraffin to a liquid-liquid extraction zone and therein subjecting said feed to extraction conditions with a mixed solvent system composed of 70-90% of a sulfolane and 30-10% of a ketone to form a raffinate containing the paraffins and an extract containing the olefins,
    (b) passing said extract to a separation zone and therein contacting same with water to form an upper olefin-containing phase and a lower solvent phase containing water and separately removing each of said phases from said separation zone,
    (c) heating said solvent phase and introducing said heated solvent phase into a drying zone operated under conditions to remove an overhead stream comprising water and some ketone and a bottoms stream comprising solfolane and ketone solvent, and
    (d) returning at least a portion of said lower solvent phase as vapor to a lower portion of said drying zone to serve as a stripping medium to regenerate said heated solvent by removing water therefrom and form said overhead stream.

2. A method according to claim 1 wherein said solvent mixture is sulfolane and methyl ethyl ketone.

3. A method according to claim 1 wherein said olefin is octene-1 and paraffin is n-octane.

4. A method according to claim 1 wherein a portion of said upper olefin phase is returned as reflux to the extraction zone in (a) and the overhead stream in (c) is cooled and condensed and at least a portion of the condensate formed is returned as reflux to an upper portion of said drying zone.

5. A method according to claim 4 wherein said solvent mixture is sulfolane and methyl ethyl ketone and said olefin is octene-1 and paraffin is n-octane.

* * * * *